United States Patent [19]
Willenberg et al.

[11] Patent Number: 4,694,112
[45] Date of Patent: Sep. 15, 1987

[54] PROCESS FOR PRODUCING 2,2,2-TRIFLUOROETHANOL

[75] Inventors: Heinrich Willenberg, Garbsen; Wilhelm Pohlmeyer; Werner Rudolph, both of Hanover, all of Fed. Rep. of Germany

[73] Assignee: Kali-Chemie Aktiengesellschaft, Hanover, Fed. Rep. of Germany

[21] Appl. No.: 837,824

[22] Filed: Mar. 10, 1986

[30] Foreign Application Priority Data

Mar. 26, 1985 [DE] Fed. Rep. of Germany ....... 3510883

[51] Int. Cl.$^4$ .............................................. C07C 31/38
[52] U.S. Cl. .................................................... 568/842
[58] Field of Search ......................................... 568/842

[56] References Cited

U.S. PATENT DOCUMENTS 3,356,747 12/1967 Anello et al. ........................ 568/842
4,072,726 2/1978 Nychka et al. .

FOREIGN PATENT DOCUMENTS 0175558 3/1986 European Pat. Off. .
0011376 3/1980 Japan ..................................... 502/55
8203854 11/1982 PCT Int'l Appl. .

OTHER PUBLICATIONS

Kostrov et al, C.A. 69 (1968), 70327k.

Primary Examiner—Howard T. Mars
Attorney, Agent, or Firm—Schwartz, Jeffery, Schwaab, Mack, Blumenthal & Evans

[57] ABSTRACT

A catalytic process for producing 2,2,2-trifluoroethanol by gas phase hydrogenation of 2,2,2-trifluoroethyl trifluoroacetate using oxide catalysts formed of copper and zinc and containing 0 to 10 percent chromium oxide.

15 Claims, No Drawings

PROCESS FOR PRODUCING
2,2,2-TRIFLUOROETHANOL

BACKGROUND OF THE INVENTION

The present invention relates to a process for producing 2,2,2-trifluoroethanol (TFE) by catalytic hydrogenation of 2,2,2-trifluoroethyl trifluoroacetate with elemental hydrogen in the gaseous phase.

2,2,2-trifluoroethanol has a high thermal stability and, in certain mixture proportions with other materials, outstanding thermodynamic characteristics. Thus, it may be used in admixture with water as a working fluid in heat engines (for example, as "Fluorinol 85", a mixture of 85 mole percent, 2,2,2-trifluoroethanol and 15 mole percent water). Because of its special chemical properties, 2,2,2-trifluoroethanol may serve as a solvent (for example for polyamides and polypeptides) as well as a reactant (for example in the production of anesthetics). It can also be used as a reaction medium (for example, for photolytic reactions).

It is known that 2,2,2-trifluoroethanol can be produced by molecule cleaving hydrogenation of 2,2,2-trifluoroethyl trifluoroacetate with elemental hydrogen in the gaseous phase in the presence of catalytically active solid materials, that is to say by heterogenous catalysis. Two moles of alcohol are thereby produced from one mole of ester and two moles of hydrogen.

German Patent No. DE-PS 12 71 696 describes such a process which is carried out at temperatures between 225° and 400° C. and at pressures between 1 and 5 bar absolute, whereby either chromite solid catalysts or noble metal supported catalysts are utilized as the catalysts. Materials utilized as solid catalysts include, for example, copper chromite, zinc chromite, iron chromite and manganese chromite, or mixtures of oxides and chromites. The weight ratio of chromium oxide to other metal oxide may lie between 0.5:1 and 10:1.

Because known examples of noble metal supported catalysts produce only very low conversions or selectivity, only the chromite solid catalysts are relevant for practical economic application. However, contact with a catalyst material formed of chromium oxide and zinc oxide yields unsatisfactory results. The selectivity in particular may be increased by additions of copper oxide and calcium oxide (weight ratio of $Cr_2O_3/ZnO=0.4:1$ and $Cr_2O_3/CuO=1.6:1$). The relatively best results with reference to the catalyst life, conversion and selectivity are achieved with catalyst of chromium oxide, copper oxide and barium oxide (weight ratio of $Cr_2O_3/CuO=1.1:1$).

However, the required reaction temperatures of well above 200° C. and the short lifetimes of at most 27 hours (with correspondingly low catalyst yields) are of little utility for technical applications. In addition, the use of such chromite catalysts with high chromium oxide contents is undesirable for a number of reasons (e.g. waste water disposal problems, carcinogenicity, etc.).

According to U.S. Pat. No. 4,072,726 a chrome-free, copper catalyst containing 50 to 100 weight percent copper oxide and 0 to 50 weight percent of an inert binder can be used to effect the same conversion under comparable temperature and pressure conditions. According to the examples given therein, at copper oxide contents between 75 and 95 weight percent and a reaction temperature of 235° C., reaction times of 53 to 175 hours, conversions of over 54 percent and a selectivity of at least 95 percent are obtained. The corresponding catalyst yields lie between 19 and 42 kg of 2,2,2-trifluoroethanol per kilogram of catalyst.

Despite the substantially longer duration of the reaction and higher catalyst yields in comparison to the results of German Patent No. DE-PS 12 71 696, the required reaction temperatures, which likewise are significantly above 200° C., and the extremely high copper oxide content, which leads to a notable increase in the cost of the catalyst, constitute disadvantages which cannot be overlooked.

High temperatures and high copper contents additionally increase the susceptability to thermal aging, for example by recrystallization and sintering, particularly when the synthesis gas contains traces of chlorine compounds (Ullman, Vol. 3, p. 545, 4th ed., 1976). This is, however, always the case in technical processes where the 2,2,2-trifluoroethyl trifluoroacetate is produced as initially described in U.S. Pat. No. 4,072,726 by reacting the corresponding acid chloride with 2,2,2-trifluoroethanol.

SUMMARY OF THE INVENTION

It is the object of the invention to provide a new process for producing 2,2,2-trifluoroethanol by catalytic hydrogenation of trifluoroethyl trifluoroacetate with elemental hydrogen in the gaseous phase.

Another object of the invenion is to provide a process for producing 2,2,2-trifluoroethanol which can be carried out at lower reaction temperatures.

A further object of the invention is to provide a process for producing 2,2,2-trifluoroethanol which utilizes a lower cost catalyst.

It is also an object of the invention to provide a process for producing 2,2,2-trifluoroethanol which is less subject to the waste water disposal and carcinogenicity problems associated with catalysts having high chromium oxide contents.

Yet another object of the invention is to provide a process for producing 2,2,2-trifluoroethanol which produces a high conversion with good selectivity.

A still further object of the invention is to provide a process for producing 2,2,2-trifluoroethanol which has a long catalyst lifetime and results in high catalyst yields.

These and other objects of the invention are achieved by providing a process for producing 2,2,2-trifluoroethanol comprising catalytically hydrogenating 2,2,2-trifluoroethyl trifluoroacetate with elemental hydrogen in the gaseous phase in the presence of a catalytically effective amount of a metal oxide catalyst comprising zinc oxide and copper oxide wherein the weight ratio of chromium oxide to the total of the oxides is from 0 to 0.1:1. The catalyst may optionally contain amounts of iron oxide, chromium oxide, manganese oxide, calcium oxide, aluminum oxide and/or silicon oxide. The sum of all the oxides is equal to 100 percent by weight.

DETAILED DESCRIPTION OF PREFERRED EMBODIMENTS

The process of the invention is based on the production of 2,2,2-trifluoroethanol by catalytic hydrogenation of 2,2,2-trifluoroethyl trifluoroacetate with elemental hydrogen in the gaseous phase in the presence of a metal oxide catalyst and is characterized in that the catalyst is made of zinc oxide and copper oxide as well as optional amounts of iron oxide, chromium oxide, manganese oxide, calcium oxide, aluminum oxide and- /or silicon oxide. The sum of all the oxides is 100 weight percent, and the weight ratio of chromium oxide to the total of the oxide components is from 0 to 0.1:1, preferably 0 to 0.5:1.

Preferably the catalyst contains from 10 to 90 weight percent zinc oxide and from 10 to 90 weight percent copper oxide, most preferably from 10 to 60 weight percent zinc oxide and from 10 to 60 weight percent copper oxide.

In one embodiment of the process of the invention the catalyst may consist entirely of zinc oxide and copper oxide. In another embodiment of the process of the invention the catalyst additionally contains oxides of iron, chromium, manganese, calcium, aluminum and/or silicon. In this latter embodiment the aluminum oxide content may particularly be from 0 to 40 weight percent while the content of the other oxides in each case may be from 0 to 5 weight percent.

Contact catalysts in which zinc oxide and copper oxide together constitute over 50 weight percent of the catalyst are especially preferred.

Known catalyst materials can be utilized for the process of the invention. Preferred catalysts are those which are produced starting from a mixed crystal precursor with common, easily decomposable anions, such as carbonate, formate or oxalate. A high degree of dispersion of the active components can thereby be achieved (Ullmann, Vol. 13, pp. 528 and 559, 4th ed., 1976).

Copper-zinc catalysts are known for use in the production of methanol from carbon monoxide, carbon dioxide and hydrogen in the so-called low pressure process. The temperatures and pressures used thereby lie in the range from 230° to 280° C. and 50 to 100 bar (Ullmann, Vol. 16, pp. 624 et seq., 4th ed., 1976). There are no hints to be found anywhere, however, that catalysts of this type are suitable for molecule cleaving hydrogenation of esters. It was also not to be expected that the working range of these contact catalysts could lie below 230° C. or 50 bar.

Surprisingly, copper-zinc catalysts of the aforedescribed type are outstandingly suitable for gas phase catalytic hydrogenation of 2,2,2-trifluoroethyl trifluoroacetate with elemental hydrogen, and indeed, the reaction can be carried out in the temperature range between 100° and 230° C. and in the pressure range between 1 and 5 bar (absolute).

In one particular embodiment of the process, temperatures between 120° and 210° C. and pressures between 1.5 and 2.5 bar (absolute) are advantageously utilized. In order to achieve an optimum degree of conversion, the reactor temperature is thereby continuously increased during the course of the reaction while the pressure is held substantially constant.

The empty vessel residence time should amount to from 5 to 50 seconds under the selected temperature and pressure conditions. Preferably the residence time may be from 10 to 25 seconds.

The mole ratio of hydrogen to the ester may be less than stoichiometric, stoichiometric or greater than stoichiometric. Desirably, the ratio should not fall below 1.5:1 and should not exceed 3.5:1. In the initial phase, the less than stoichiometric range will more likely be chosen because of the particularly high activity of the fresh, as yet unused contact catalyst material, and the ratio will first be increased later in course of time. The preferred mole ratio during the main production phase advantageously lies between 2:1 and 3:1.

The process of the invention also includes a cyclically operating embodiment in which hydrogenation and catalyst regeneration are alternately carried out. This embodiment is characterized by cyclic operation of the process in which:
(a) the hydrogenation is carried out, optionally with progressive increase of the temperature, until the conversion falls off,
(b) the catalyst is regenerated in situ with water, and thereafter
(c) a new hydrogenation/regeneration cycle begins corresponding to the steps (a) and (b).

To regenerate the catalyst, water is used in liquid or vapor form, perferably in vapor form. The use of water in liquid form to reactivate a catalyst is based according to the prior art on a deactivation caused by poisoning which is generally at least partially reversible.

However, with the aforedescribed copper-zinc catalysts, even after complete removal of the chloride (originating from the tiniest chloride content in the 2,2,2-trifluoroethyl trifluoroacetate which is used) by means of a polar organic solvent such as 2,2,2-trifluoroethanol or methanol, no reactivation of the catalyst contact material occurs. Surprisingly, a regeneration of the catalyst is first achieved by supplemental (i.e. simultaneously or successively carried out) treatment with water or water vapor or by treatment only with water or water vapor. This may possibly be due to at least partial reversal of the water loss caused by aging.

Advantageously, the regeneration is carried out in situ, i.e. in the reaction vessel, because then removal of the catalyst from the reactor and the possibly necessary surface passivation of the pyrophoric, reduced contact material by oxidation may be omitted. It is understood, however, that it is also possible to carry out the regeneration after transferring the aged catalytic contact material into a separate container, i.e. a so-called regenerator.

The following examples are intended to illustrate the process of the invention in further detail without limiting its scope.

EXAMPLES

In the examples commercially available catalysts formed of carbonate material (tablets of approximately 5 mm height and diameter) were used which had the composition given in the table. In listing the composition of the catalyst, the proportions are listed as metal oxides. Constituents present only in trace amounts (for example, sodium or potassium) are thereby not taken into account just as anion constituents (for example, carbonate or hydroxide) and water. After filling of the reaction vessel provided with a heating jacket, the contact material in the vessel was activated according to prescribed procedure by carefully reducing it with a hydrogen-nitrogen mixture (1 to 100 volume percent $H_2$) at temperatures up to approximately 250° C.

REACTION

Thereafter vaporized 2,2,2-trifluoroethyl trifluoroacetate (in the form of its azeotrope with 2,2,2-trifluoroethanol) and elemental hydrogen were introduced together, and the reaction of the two reactants to produce 2,2,2-trifluoroethanol took place under the reaction conditions listed in the following table. During the course of the reaction, the reaction temperature was continuously increased by increasing the temperature of the oil bath which heats or cools the reaction vessel by means of the heating jacket. The conversion thereby passed through a maximum while the selectivity varied between 95 and 100 mole percent. In the course of the reaction the molar ratio of hydrogen ($H_2$) to the ester was increased in accordance with the decrease in activity of the catalyst. In the table the average mole ratio is given.

REGENERATION

In examples 2.1 or 3.1 and 3.2 a regeneration was carried out in each case after the reaction in order to be able to follow with a further (second or third) cycle with the same catalyst charge. This process always took place in situ, i.e. in the reaction vessel, whereby the liquid medium was circulated by pumping at room temperature through the catalyst charge and the gaseous medium (water vapor) was passed through the catalyst charge while the reactor was being heated. The chloride content expected from material balance considerations was found in the liquid medium.

After example 2.1, regeneration was carried out at room temperature with a liquid mixture of trifluoroethanol and water. After example 3.1, regeneration was carried out at room temperature with waer, and after example 3.2 with waer vapor at a temperature in the vicinity of the reaction temperature. Attempts to regenerate the catalyst under similar conditions using only trifluoroethanol or methanol did not produce satisfactory regeneration.

TABLE

| Example Identifying Data | 1 | 2.1. | 2.2. | 3.1. | 3.2. | 3.3. |
|---|---|---|---|---|---|---|
| Catalyst: | | | | | | |
| Wt. % CuO | 44 | 43 | same as 2.1. | same as 2.1. | same as 2.1. | same as 2.1 |
| Wt. % ZnO | 21 | 54 | " | " | " | " |
| Wt. % $Al_2O_3$ | 31 | 3 | " | " | " | " |
| Wt. % $Cr_2O_3$ | 4 | — | " | " | " | " |
| Catalyst Charge No. | 1 | 2 | 2 | 3 | 3 | 3 |
| Cycle No. | 1 | 1 | 2 | 1 | 2 | 3 |
| Reaction: | | | | | | |
| Chloride ppm by wt.* | 200 | 200 | 200 | 20 | 20 | 20 |
| Pressure (bar abs.) | 2 | 2 | 2 | 2 | 2 | 2 |
| Residence Time (sec.)** | 11–15 | 12–15 | 12–15 | 12–15 | 12–15 | 12–13 |
| Mole Ratio $H_2$/Ester | 2.9 | 2.8 | 2.8 | 2.8 | 2.8 | 2.8 |
| Temperature (°C.) | 125–200 | 115–210 | 150–200 | 120–200 | 150–204 | 155–205 |
| Maximum Conversion (Mole %) | 55 | 72 | 45 | 77 | 45 | 39 |
| Reaction Duration (hr.) | 121 | 186 | 121 | 221 | 116 | 64 |
| Catalyst Yield (kg TFE/kg Catalyst) | 44 | 44 | 25 | 67 | 20 | 13 |

*in the ester or azeotrope feed
**empty vessel residence time at the indicated pressure and temperature The foregoing description and examples have been set forth merely to illustrate the invention and are not intended to be limiting. Since modifications of the described embodiments incorporating the spirit and substance of the invention may occur to persons skilled in the art, the scope of the invention should be limited solely with respect to the appended claims and equivalents.

What is claimed is:

1. A process for producing 2,2,2-trifluoroethanol by catalytic hydrogenation of 2,2,2-trifluoroethyl trifluoroacetate with elemental hydrogen in the gaseous phase at a reaction temperature of at least 100° C. and less than 210° C. in the presence of an oxide catalyst comprising oxides of zinc and copper, the sum of all oxides being set at 100 percent and the weight ratio of chromium oxide to the total of the oxide materials being from 0 to 0.05:1.

2. A process according to claim 1, wherein said catalyst further comprises at least one oxide selected from the group consisting of oxides of iron, chromium, manganese, calcium, aluminum and silicon.

3. A process according to claim 1, wherein the catalyst comprises from 10 to 90 weight percent zinc oxide and from 10 to 90 weight percent copper oxide.

4. A process according to claim 3, wherein the catalyst comprises from 10 to 60 weight percent zinc oxide and from 10 to 60 weight percent copper oxide.

5. A process according to claim 1, wherein the catalyst comprises from 0 to 40 weight percent aluminum oxide.

6. A process according to claim 2, wherein the catalyst comprises from 0 to 5 weight percent of at least one oxide selected from the group consisting of oxides of iron, chromium, manganese, calcium, and silicon.

7. A process according to claim 6, wherein said at least one oxide is selected from oxides of chromium, calcium and silicon.

8. A process according to claim 1, wherein the total pressure is from 1 to 5 bar (absolute).

9. A process according to claim 8, wherein the total pressure is from 1.5 to 2.5 bar (absolute).

10. A process according to claim 1, wherein the empty reactor residence time under the prevailing reactor conditions is from 5 to 50 seconds.

11. A process according to claim 10, wherein the residence time is from 10 to 25 seconds.

12. A process according to claim 1, wherein the mole ratio of hydrogen to the ester is from 1.5:1 to 3.5:1.

13. A process according to claim 12, wherein the mole ratio of hydrogen to the ester is from 2:1 to 3:1.

14. A process according to claim 1, wherein the process is carried out cyclically by:
   (a) carrying out the hydrogenation until the conversion falls off;
   (b) regenerating the catalyst in situ with water, and thereafter
   (c) beginning a new hydrogenation/regeneration cycle according to steps (a) and (b).

15. A process according to claim 14, wherein the temperature of the hydrogenation reaction is increased as the activity of the catalyst decreases.

* * * * *